(12) United States Patent
Ugalde et al.

(10) Patent No.: US 6,682,914 B2
(45) Date of Patent: Jan. 27, 2004

(54) BIOACTIVE TETRACYCLIC DITERPENE COMPOUNDS AND METHODS OF PREPARATION AND USE THEREOF

(75) Inventors: Unai Ugalde, Hondarribia (ES); Tomas Roncal, San Sebastian (ES); Olov Sterner, Malmoe (SE)

(73) Assignee: Universidad del Pais Vasco/Euskal Herriko Unibersitatea, Leioa (ES)

( * ) Notice: Subject to any disclaimer, the term of this patent is extended or adjusted under 35 U.S.C. 154(b) by 0 days.

(21) Appl. No.: 09/999,193

(22) Filed: Oct. 31, 2001

(65) Prior Publication Data

US 2003/0087966 A1 May 8, 2003

(51) Int. Cl.$^7$ .............................. C12N 3/00; C12N 1/36; C12N 1/38; C12N 1/18; C12P 33/00
(52) U.S. Cl. ...................... 435/142; 435/244; 435/245; 435/256.1; 435/256.3
(58) Field of Search ........................... 435/256.3, 256.1, 435/242, 244, 245

(56) References Cited

PUBLICATIONS

Thomas H. Adams et al., "brlA Is Necessary and Sufficient to Direct Conidiophore Development in *Aspergillus nidulans*," Cell (1988), vol. 54, pp. 353–362.
A.J. Clutterbuck, "A Mutational Analysis of Conidial Development in *Aspergillus Nudulans*," Genetics (1969), vol. 63, pp. 317–327.
J.W. Foster et al., "Microbiological Aspects of Penicillin," Journal of Bacteriology (1945), vol. 50, pp. 365–368.
Jillian C. Galbraith et al., "Sporulation of *Aspergillus niger* in Submerged Liquid Culture," Journal of General Microbiology (1969), vol. 59, pp. 31–45.
G. Hadley et al., "The Sporulation of *Penicillium notatum* Westling in Submerged Liquid Culture," Journal of Experimental Botany (1958), vol. 9(27), pp. 418–425.
I.B. Heath, ed., "Tip Growth in Plant and Fungal Cells," Academic Press, San Diego, California (1990), pp. v–x and 1–29.
Peter M. Mirabito et al., "Interactions of Three Sequentially Expressed Genes Control Temporal and Spatial Specificity in Aspergillus Development," Cell (1989), vol. 57, pp. 859–868.
A.G. Morton, "The Induction of Sporulation in Mould Fungi," Proceedings of the Royal Society [Biol] (1961), vol. 153, pp. 548–569.
S. Pascual et al., "Induction of submerged conidiation of the biocontrol agent *Penicillium oxalicum*," Applied Microbiology and Biotechnology (1997), vol. 48, pp. 389–392.
J.E. Smith et al., "An introduction to Biochemistry of Fungal Development," Academic Press, New York (1974), pp. 156–210.
U. Ugalde et al., "Morphology and Calcuim–Induced Conidiation of *Penicillium Cyclopium* in Submerged Culture," Transactions of the British Mycological Society (1983), vol. 80(2), pp. 319–325.
Jenny Wieser et al., "Genetic requirements for initiating asexual development in *Aspergillus nidulans*," Current Genetics (1994), vol. 27, pp. 62–69.

Primary Examiner—Herbert J. Lilling
(74) Attorney, Agent, or Firm—Katten Muchin Zavis Rosenman

(57) ABSTRACT

Newly-isolated and purified metabolites which are effective in regulating the development of at least one filamentous fungal microorganism species are disclosed. These compounds, which are referred to as conidiogenol and conidiogenone, may be used to induce conidiation in and/or to inhibit the growth of populations of such fungal species. The compounds are preferably produced by culture of the fungal species *Penicillium cyclopium*, and may be subsequently recovered from the culture medium and purified. Methods of using and methods of producing these compounds are also disclosed.

36 Claims, 1 Drawing Sheet

BIOACTIVE TETRACYCLIC DITERPENE COMPOUNDS AND METHODS OF PREPARATION AND USE THEREOF

TECHNICAL FIELD

The present invention relates broadly to the isolation, identification and use of natural products. More particularly, this invention relates to substantially pure forms of two related biologically active diterpenoid compounds that are useful to regulate the development of microorganisms. Specifically, these substances may be used to induce conidiation in, and thereby also to inhibit the growth of, such microorganisms.

BACKGROUND OF THE INVENTION

The continuous deposition of new cell wall and plasma membrane material at a fixed cellular site (termed "apical extension") is a successful growth pattern which is widely observed in prokaryotic and eukaryotic organisms (Heath, 1990). The derived tubular structure (the hypha) offers great practical advantages for the colonization of solid substrates, as well as the undertaking of fungal infection. It acts as a device providing sheer physical force combined with a versatile arsenal of apically secreted enzymes directed at the hydrolysis of biopolymers and other bioconversions. However, apical extension growth is unsuitable for dispersive purposes or resistance to unfavorable environmental conditions, and filamentous microorganisms have evolved alternative morphogenetic programs to generate cell forms which cater to these requirements: spores (Smith and Berry 1974).

The formation of conidia or asexual spores among filamentous fungi is a complex process in which a succession of precisely regulated cellular events take place in tight coordination. Environmental or endogenous stimuli are thought to trigger a set of genetically determined programs which lead to the cessation of apical growth, and to the development of reproductive asexual structures which finally result in the formation of conidia.

Significant advances in the knowledge of the genes controlling conidial development have been carried out in the last two decades, using mainly *Aspergillus nidulans* as model organism. Three regulatory genes: brlA, abaA and wetA (Clutterbuck, 1969; Mirabito et al., 1989) are involved, and brlA (coding for a transcription factor) occupies a central position in the control of development. Its expression is sufficient (and therefore necessary) for the initiation of conidial development in *Aspergillus nidulans* (Adams et al., 1988). Besides these, other early acting genes have been identified, which are necessary for the activation of brlA: flbA, flbB, flbC, flbD, flbE and fluG (Wieser et al., 1994). However, little is known about the factors which trigger the process of conidial development and the mechanism that is followed before the first gene is activated. It is suspected that an environmental stimulus or set of stimuli are perceived by the fungus, leading to the triggering of a signal transduction system which, in turn, activates the conidiation program.

The environmental stimuli reportedly implicated in the induction of conidiation have been a matter of investigation since the pioneering works of Sir Hans Klebs (1896). They include: emergence to the atmosphere, nutrient depletion (especially the nitrogen source), presence of cations, temperature, light stimulation and pH changes in the medium. However, the precise way in which these diverse stimuli influence the process in different fungi, or their mechanism of action, remains in the realm of hypothesis.

Without doubt the most widespread and powerful stimulus leading to conidiation is the emergence to the aerial environment (Morton, 1961) and several mechanisms have been proposed to explain what happens in this case (oxidative stress and desiccation). However, no definitive demonstration of the validity of one or more of these mechanisms has emerged. In any case, changes in surface characteristics of hyphae are known to occur on emergence (Morton, 1961), which could be related to the induction mechanism, but no modern studies on this effect have been pursued.

Contrary to the widespread subaerial conidiation among filamentous fungi, conidiation in submerged culture is a relatively rare event in fungal cultures, and is difficult to induce through manipulations of the culture conditions in the best cases (Morton, 1961; Galbraith and Smith, 1969). Controlled nutrient limitation or the addition of special agents which have been empirically shown to function as inducers is a common strategy. One such example is the addition of calcium ions.

Fungi belonging to the genus Penicillium respond to the addition of calcium in liquid culture with a precisely timed morphogenetic program leading to conidiation (Foster et al., 1945, Hadley and Harrold, 1958; Ugalde and Pitt, 1983; Pascual et al., 1997), in a way indistinguishable from that occurring spontaneously in subaerial culture. The mode of action of the cation, as well as the changes taking place at the cellular level as a result of its action, have been extensively studied for the last twenty years. The results of this research support the view that the mode of action of the cation is unrelated to entry and subsequent rise in cytosolic calcium levels, but is mediated through an interaction taking place at the cell surface.

Conidia produced by filamentous fungi such as those belonging to the genus Penicillium and to other genera as well can be harvested and employed in various useful ways. For example, such conidia can be employed in fungicides, herbicides and insecticides, and they can also be employed as biotransformation agents or as catalysts in chemical reactions; they are also useful as additives in the food industry since, for example, strains of the genus Penicillium are used in the production of Roquefort cheese and Danish blue cheese, and strains of the genus Aspergillus are widely used in fermentation processes for the production of enzymes and fermented foods. Thus, further elucidation of the mechanisms leading to conidiation, and of the events and molecules that trigger it, would have potential commercial significance in several major industries.

Moreover, since the formation of conidia leads to (or occurs in tandem with) the cessation of apical growth, further elucidation of the mechanisms leading to conidiation, and of the events and molecules that trigger it, would have potential biomedical significance as a means of fungal control. In particular, the isolation and purification of the molecular substances that induce conidiation would be useful as a means of inhibiting or even preventing invasive and/or infectious fungal growth, and also could potentially lead to the design of analogs of such molecules which, conversely, could be used to inhibit conidiation and thereby stimulate or even enhance fungal growth. However, the prior art is deficient in any description of such biologically active (or "bioactive") substances.

It is therefore an object of the present invention to fulfill a long-standing need and desire in the art and to provide bioactive substances having conidiation-inducing activity.

SUMMARY OF THE INVENTION

Briefly, the invention relates to substantially pure forms of hitherto unknown secondary metabolites of microorganism strains belonging to the genus Penicillium, and likely to other genera as well. These metabolites are tetracyclic diterpenoid compounds, and in one embodiment of the present invention there are provided tetracyclic diterpene compounds isolated from *Penicillium cyclopium* having the following general structural formula (I):

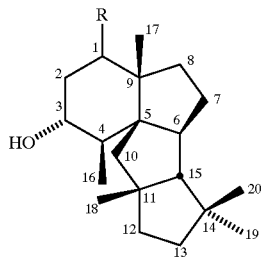

wherein R stands either for —OH (hydroxyl) or =O.

In another more specific embodiment of the present invention there is provided a compound isolated from *Penicillium cyclopium* having the following structural formula (1):

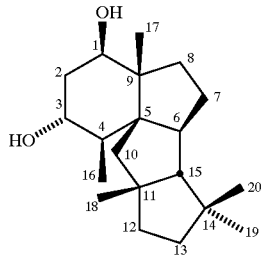

In yet another more specific embodiment of the present invention there is provided a compound isolated from *Penicillium cyclopium* having the following structural formula (2):

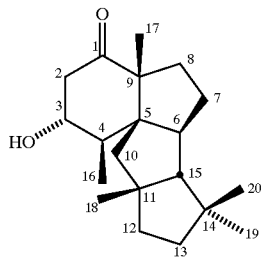

Spectral data obtained for compounds (1) and (2) were in agreement with the structure shown in formula (I). It was found that these compounds efficiently induce conidiation not only in the producer microorganism *P. cyclopium*, but also in other members of the genus Penicillium and outside that genus as well. This invention also includes the acylated derivatives of the compound having the structural formula (I).

In still other embodiments of the present invention, there are provided methods for producing, as well as methods for using, the compounds disclosed herein. In general, the method of producing these bioactive substances comprises culturing, under aerobic conditions, a strain of microorganism belonging to the genus Penicillium (or a mutant or variant thereof) capable of elaborating said bioactive substances, in a suitable nutrient medium containing at least a carbon source and a nitrogen source, at a pH and temperature, and for a time, sufficient for production of said bioactive substances, and thereafter accumulating said substances in the culture medium and isolating said substances therefrom.

The methods of use generally comprise the application of these bioactive substances, preferably in combination, as conidiation inducers, to at least one strain of microorganism, preferably one belonging to the genus Penicillium or the genus Aspergillus; the methods include any related biochemical, microbiological and clinical effects associated with the morphogenetic process, such as growth inhibition, whether or not the morphogenetic process is completed.

BRIEF DESCRIPTION OF THE DRAWINGS

These and other aspects, features, objects and advantages of the present invention will become more apparent from the following detailed description of the presently most preferred embodiments thereof (which are given for the purposes of disclosure), when read in conjunction with the accompanying drawing (which forms a part of the specification, but which is not to be considered limiting in its scope), wherein.

DETAILED DESCRIPTION OF THE PREFERRED EMBODIMENT

Figure 1:
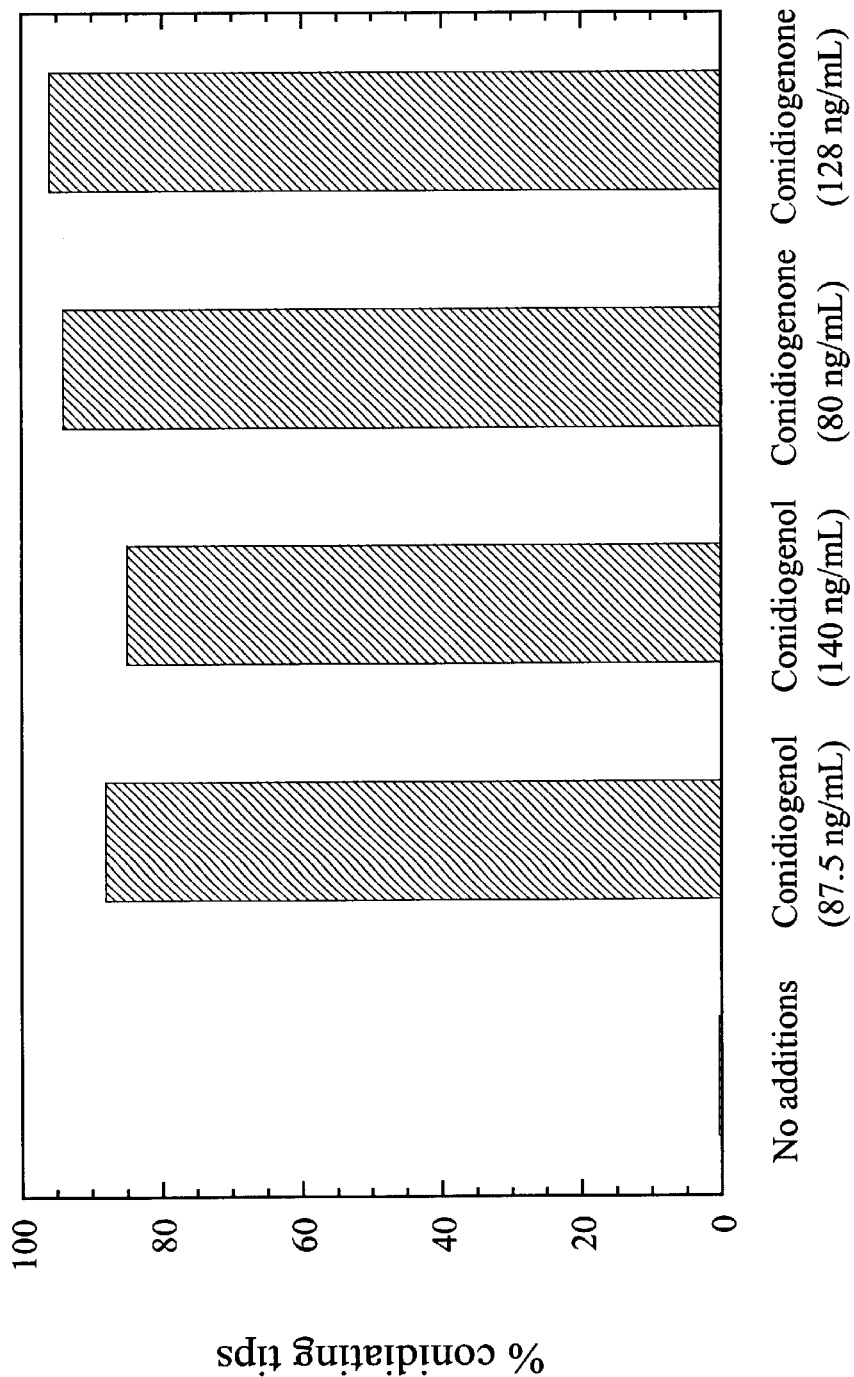
FIG. 1 is a bar graph illustrating the conidiation-inducing effect of the compounds of the present invention in *Penicillium cyclopium* cultured under submerged conditions.

As stated hereinabove, the present invention is directed toward the isolation and identification of hitherto unknown compounds. More specifically, the present invention isolates, identifies and characterizes the structures and biological activity of the two diterpenoid compounds (1) and (2). These compounds possess biochemical action in the nature of conidiation-inducing properties.

Most specifically, compound (1) (the substance having the structure of formula (I) wherein R is —OH (hydroxyl)) has the molecular formula $C_{20}H_{34}O_2$, and has been assigned the systematic name (1R*, 3R*, 7R*, 8S*, 11R*, 12R*, 14S*, 15R*)-3,6,6,11,15-pentamethyl-tetracyclo[$9.4.0.0^{1,8}.0^{3,7}$]-pentadecan-12,14-diol (based upon spectral data). Compound (1) has also been denominated, and will sometimes hereinafter be referred to as, "conidiogenol." Based upon spectral data, compound (2) (the substance having the structure of formula (I) wherein R is =O) has the molecular formula $C_{20}H_{32}O_2$, and has been assigned the systematic name (1R*, 3R*, 7R*, 8S*, 11R*, 14S*, 15R*)-14-Hydroxy-3,6,6,11,15pentamethyl-tetracyclo[$9.4.0.0^{1,8}.0^{3,7}$]-pentadecan-12-one. Compound (2) has also been denominated, and will sometimes hereinafter be referred to as, "conidiogenone." While both compound (1) and compound (2) are tetracyclic diterpenes, the spatial geometry of each molecule, i.e., the precise spatial arrangement of the carbon atoms, is still unknown but is believed to be unprecedented and therefore novel.

These compounds are preferably isolated from the fungal species *Penicillium cyclopium*, although the strain of microorganism from which they may be isolated is not particularly restricted to that species, provided that the strain belongs to the genus Penicillium and is capable of producing conidiogenol and conidiogenone. The microorganism *Penicillium*

*cyclopium* strain Westling (IMI 229034) is a preferred strain to use to produce these substances, primarily because that strain produces conidiogenol and conidiogenone very efficiently. That strain is deposited with the International Mycological Institute under the accession number IMI 229034. However, in the practice of the invention, variants and spontaneous or artificial mutants of the *Penicillium cyclopium* Westling strain, as well as variants and spontaneous or artificial mutants of other strains of the genus Penicillium which are capable of producing conidiogenol and conidiogenone, whether such artificial mutants are created by conventional, physical or chemical means, or by recombinant genetic engineering techniques, can be employed with success.

In the present invention, conidiogenol and conidiogenone can be produced by inoculating a nutrient medium with said conidiogenol- and conidiogenone-producing strain of microorganism, and thereafter incubating the inoculated medium in accordance with any aerobic culturing method generally used for fungi. Any nutrient medium containing assimilable sources of carbon and nitrogen and, if required, an inorganic salt, can be used. Examples of assimilable carbon sources include but are not limited to glucose, fructose, sucrose, starch, dextrin, glycerol, maltose and organic acids, which may be used alone or in combination with one another. Examples of assimilable nitrogen sources include but are not restricted to organic nitrogen sources such as corn steep liquor, peptone, yeast extract, meat extract, caseine, amino acids or urea, and inorganic nitrogen sources such as nitrate salts or ammonium salts, any of which may be used alone or in combination with one another. The inorganic salt, if required, preferably is selected from among the sulfate and phosphate salts of sodium, potassium, calcium or magnesium.

If necessary, the nutrient medium may be supplemented with heavy metal salts such as salts of iron, copper, zinc, manganese or molybdenum, etc., and/or with vitamins such as biotin, riboflavin, etc., and/or with other organic or inorganic substances for assisting in the growth of the microorganism and promoting the production of both conidiogenol and conidiogenone, as is well known in the art. If necessary, the nutrient medium may be further supplemented with an anti-foaming agent or a surfactant, such as silicone oil, vegetable oil, polyalkylene glycol ethers, and the like, in accordance with known methods.

Cultivation of said conidiogenol- and conidiogenone-producing strain in the nutrient medium can be carried out by any routine aerobic culturing technology for incubating microorganisms for the production of bioactive substances. Preferred is a liquid culturing method, particularly a shake culture or a submerged aerobic culture.

The cultivation is usually carried out in the temperature range of 15° C. to 30° C., preferably at 20° C.–28° C., and the pH of the medium is generally between 3 and 8, and preferably in the range of 4.5–5. Conidiogenol and conidiogenone are accumulated in the medium by culturing for 1–3 days, and when maximum production of conidiogenol and conidiogenone are obtained, cultivation can be terminated.

As is well known in the art, these culturing conditions, such as the composition of the medium, pH of the medium and culturing temperature, as well as other conditions such as the agitation speed and aeration rate, can be varied, depending upon the microorganism strain used and the atmospheric conditions, in order to obtain the most preferable result.

During such cultivation, conidiogenol and conidiogenone accumulate both in the culture medium and in the mycelia. However, for several reasons, these substances are preferably isolated only from the culture medium. First, the quantity of these substances that can be obtained from the mycelia is extremely low, because these molecules accumulate primarily in the culture medium. Second, when the compounds are extracted from a mycelium, it has been found that the extracted substances will foul the laboratory equipment (e.g., filters and columns), whereas it has been found that no such technical difficulties are encountered when these substances are extracted from the culture medium. These two reasons are strong indicators that extraction from the mycelia should be avoided, and therefore at this point in the extraction process the mycelia are preferably separated from the culture medium by filtration or centrifugation. Thereafter, by taking advantage of the physicochemical properties and biological characteristics of these bioactive substances, the conidiogenol and conidiogenone accumulated in the culture medium can then be separated from the broth and, where necessary, be further purified.

The separation can be accomplished by extracting the culture medium with a water-immiscible organic solvent such as ethyl acetate, butyl acetate or chloroform. Separation of conidiogenol and conidiogenone from the culture medium can also be achieved by the procedure which comprises contacting the medium with an adsorbent stationary phase to let both conidiogenol and conidiogenone be adsorbed, and by thereafter eluting those bioactive substances from the stationary phase with a solvent. The stationary phase may comprise, but is not limited to, chemically bonded silica gels such as octadecylated, octylated, or phenylated silica gels, and adsorbent resins. The solvent can be used either singly or in a combination of two or more species, according to the type and properties of the stationary phase selected. Thus, for example, aqueous solutions of water-soluble organic solvents, such as aqueous acetonitrile and aqueous alcohols, can be used.

In the present invention, a crude extract containing both conidiogenol and conidiogenone thus separated from the culture medium can be further purified as desired. This purification can be carried out by the technology used generally in the separation and purification of lipid-soluble bioactive substances, for example by column chromatography or high performance liquid chromatography. In the case of column chromatography, a stationary phase such as silica gel, activated alumina, activated carbon, or an adsorbent resin may be used, and a suitable eluent may be chosen. For example, the eluent for use in silica gel column chromatography may be selected from among chloroform, ethyl acetate, methanol, ethanol, and water, among other solvents, and each of those solvents can be used either alone or in combination with one another. In the case of high performance liquid chromatography, the stationary phase that can be used includes but is not limited to chemically bonded silica gels such as octadecylated, octylated, or phenylated silica gels, and as the mobile phase, aqueous solutions of water-soluble organic solvents such as aqueous methanol, aqueous acetonitrile, etc. can be used.

After isolation and purification from the fermentation medium, the compounds may be chemically modified by means of the standard methods known in the art. For example in order to prepare the acylated derivatives, the compounds may be treated with any conventional acylating agent in an adequate solvent at an ambient temperature through to reflux temperature.

In accordance with the invention, and as stated hereinabove, bioactive substances of formula (I) were obtained from culture media of a microorganism belonging to the genus Penicillium. After isolation and purification, two hitherto unknown tetracyclic diterpenoid substances having some unique physicochemical properties were identified. The structural elucidation of these two new compounds was determined by means of techniques including UV absorbance spectroscopy, nuclear magnetic resonance (NMR) spectroscopy and mass spectroscopy.

Bioassay data for the compounds' conidiation-inducing properties were also obtained. Conidiogenol and conidiogenone according to the invention can be used to induce conidiation in at least one fungus belonging to the genus Penicillium. Both conidiogenol and conidiogenone may be included in a useful composition prepared for the desired application.

The following examples illustrate the manner in which the bioactive substances disclosed herein may be isolated and purified, and illustrate their bioactivity as condiation inducers. These examples are given for the purpose of illustrating various embodiments of the invention, and are not meant to limit the present invention in any fashion.

EXAMPLE 1

Thirty 10 L. fermenters, each containing 10 L. of liquid medium (sucrose, 20 g/L; $NaNO_3$, 6 g/L; $KH_2PO_4$, 1.5 g/L; $MgSO_4 \cdot 7H_2O$ 0.5 g/L; $FeCl_3 \cdot 6H_2O$, 1.936 g/L; $ZnSO_4 \cdot 7H_2O$, 1.583 g/L; $CuSO_4 \cdot 5H_2O$, 0.314 g/L; $MnSO_4 \cdot H_2O$, 0.123 g/L; and $Na_2MoO_4 \cdot 2H_2O$, 0.101 g/L), were inoculated with a suspension of conidia of *Penicillium cyclopium* Westling (IMI 229034) in Tween 20 0.02% (w/v) to a final concentration of $2.5 \times 10^6$ conidia/mL. Although for the purposes of this experiment *Penicillium cyclopium* Westling (IMI 229034) was subcultured in order to find a strain with a clear and reproducible conidiation response in liquid culture, and a single spore isolate (DSS03) which met these characteristics was employed, it is believed that any strain of *Penicillium cyclopium*, and in particular, any subculture of *Penicillium cyclopium* Westling (IMI 229034) with the aforementioned characteristics, will yield acceptable quantities of the inventive compounds.

Cultures were grown at 25° C. with an aeration rate of 6 L./min. for 2 days, and were successively filtered through filter paper and 0.45 μm pore size filters to separate a supernatant and the cellular fraction. The supernatant was then adjusted to pH 7 and each 10 L.-batch fermentation filtrate was subjected to solid phase extraction by passing through a 10 g. SUPELCLEAN LC-Phenyl column (SUPELCO). After column washing with 50 mL. 50% (v/v) aqueous methanol, retained activity was eluted with 150 mL. 100% methanol and kept at −20° C. Pooled extracts arising from 300 L. culture medium were finally evaporated to dryness, rendering 595 mg of a brown-yellowish oily residue.

This residue was then dissolved in a minimum volume of methanol and further purified by reverse phase semipreparative HPLC in a Hypersil-ODS column (10×250 mm, 5 μm particle size) under an acetonitrile/water gradient (starting mobile phase, 45% (v/v) acetonitrile; final mobile phase, 100% acetonitrile; gradient time, 30 min.; flow rate, 2.2 mL./min.; UV detector, 210 nm). Two major fractions (1) and (2) with conidiation inducing activity were collected which, after solvent evaporation, yielded two yellowish oily residues of 16.3 and 4.9 mg, respectively. The final purification step was carried out by chromatography on a $SiO_2$ column with ethyl ether as the eluent. At the end of the purification procedure 0.70 and 0.64 mg of the pure compounds (1) and (2) (conidiogenol and conidiogenone, respectively) were obtained as colorless oils.

The physicochemical properties and the spectral data of conidiogenol are given below. The analytical data revealed that the component purified by chromatography from fraction 1 is conidiogenol. Detailed analysis of the NMR data, including 1D $^1H$ and $^{13}C$ spectra as well as 2D COSY, NOESY, HMQC and HMBC spectra, revealed that conidiogenol has the chemical structure of compound (1).

(1) Mass spectrum: EIMS (70 eV), m/z (rel. int.): 306.2566 (1%, $M^+$, $C_{20}H_{34}O_2$ requires 306.2559), 288.2454 (34%, $M^+-H_2O$, $C_{20}H_{32}O$ requires 288.2453), 273 (15%), 267 (50%), 233 (29%), 204 (53%), 203 (100%), 135 (17%), 109 (22%), 95 (15%).

(2) Molecular formula: $C_{20}H_{34}O_2$.

(3) $^1H$-NMR spectrum (500 MHz in $CDCl_3$) (δ, mult., J in Hz): 3.82, dd, J=3 and 3, 1-H; 3.54, ddd, J=4.2, 11 and 11, 3-H; 2.38, ddd, J=4.6, 9.4 and 9.6, 6-H; 2.04, m, 8-Ha; 1.95, m, 2-Ha; 1.94, m, 7-Ha; 1.82, ddd, J=3.2, 10.9 and 13.8, 2-Hb; 1.79, d, J=15.2, 10-Ha; 1.76, d, J=15.2, 10-Hb; 1.72, m, 12-Ha; 1.64, m, 13-Ha; 1.62, m, 12-Hb; 1.55, m, 4-H; 1.52, m, 7-Hb; 1.47, m, 15-H; 1.44, m, 13-Hb; 1.43, m, 8-Hb; 1.26, s, 18-$H_3$; 1.20, s, 17-$H_3$; 1.10, d, J=6.5, 16-$H_3$; 1.04, s, 20-$H_3$; 0.98, s, 19-$H_3$.

(4) $^{13}C$-NMR spectrum (125 MHz in $CDCl_3$) (δ): 75.1 C-1, 73.1 C-15, 69.9 C-3, 61.3 C-5, 55.6 C-6, 54.5 C-11, 48.8 C-9, 43.6 C-4, 43.3 C-10, 42.4 C-14, 41.3 C-12, 40.2 C-13, 39.0 C-2, 38.6 C-8, 31.2 C-20, 31.0 C-18, 30.0 C-7, 27.0 C-19, 23.3 C-17, 12.6 C-16.

(5) Specific rotation: $[\alpha]_D$-20 (c 0.07 in $CHCl_3$).

(6) UV/Vis spectrum (in MeOH): No maxima above 210 nm.

(7) Appearance: colorless oil.

The physicochemical properties and the spectral data of conidiogenone are given below. The analytical data revealed that the component purified by chromatography from fraction 2 is conidiogenone. Detailed analysis of the NMR data, including 1D $^1H$ and $^{13}C$ spectra as well as 2D COSY, NOESY, HMQC and HMBC spectra, revealed that conidiogenone has the chemical structure of compound (2).

(1) Mass spectrum: EIMS (70 eV), m/z (rel. int.): 304.2403 (56%, $M^+$, $C_{20}H_{32}O_2$ requires 304.2402), 286.2289 (47%, $M^+-H_2O$, $C_{20}H_{30}O$ requires 286.2296), 271 (13%), 231 (20%), 204 (100%), 203 (59%), 154 (42%), 126 (35%), 109 (22%), 95 (15%).

(2) Molecular formula: $C_{20}H_{32}O_2$.

(3) $^1H$-NMR spectrum (500 MHz in $CDCl_3$) (δ, mult., J in Hz): 3.50, dddd, J=5, 6, 9 and 10, 3-H; 2.75, dd, J=5.8 and 14.6, 2-Ha; 2.56, ddd, J=4.3, 9 and 9, 6-H; 2.51, dd, J=9.0 and 14.6, 2-Hb; 2.36, ddd, J=9, 9 and 12.8, 8-Ha; 1.97, dddd, J=3.1, 9, 9 and 13.2, 7-Ha; 1.77, qd, J=6.5 and 10.2, 4-H; 1.74, d, J=15.1, 10-Ha; 1.72, m, 12-Ha; 1.67, m, 8-Hb; 1.65, m, 13-Ha; 1.64, m, 12-Hb; 1.60, d, J=5.0, 3-HH; 1.55, m, 7-Hb; 1.52, d, J=15.1, 10-Hb; 1.50, m, 15-H; 1.47, m, 13-Hb; 1.25, s, 18-$H_3$; 1.22, s, 17-$H_3$; 1.20, d, J=6.5, 16-$H_3$; 1.04, s, 20-$H_3$; 1.01, s, 19-$H_3$.

(4) $^{13}C$-NMR spectrum (125 MHz in $CDCl_3$) (6):213.8 C-1, 72.8 C-15, 72.7 C-3, 64.2 C-5, 59.8 C-9, 54.8 C-6, 54.4 C-11, 46.9 C-2, 44.5 C-4, 43.1 C-10, 42.5 C-14, 41.4 C-12, 40.4 C-13, 39.2 C-8, 31.2 C-7, 31.1 C-20, 30.6 C-18, 26.9 C-19, 21.6 C-17, 12.8 C-16.

(5) Specific rotation: $[\alpha]_D$-35 (c 0.06 in $CHCl_3$).

(6) UV/Vis spectrum (in MeOH): No maxima above 210 nm.

(7) Appearance: colorless oil.

EXAMPLES 2–5

Bioassays were employed both qualitatively, to determine the presence/absence of conidiation inducers, and quantitatively, to estimate either the inducer concentration present in a medium, or the conidiation time resulting from a known inducer concentration.

Assays were carried out in shaken flask cultures using 25 mL. Erlenmeyer flasks containing 5 mL. of either fresh F medium (sucrose, 20 g/L; $NaNO_3$, 6 g/L; $KH_2PO_4$, 1.5 g/L; $MgSO_4.7H_2O$, 0.5 g/L; and a trace element solution (Hadley & Harrold (1958)), or the corresponding mF medium (medium which has already supported growth by the organism), adjusted to pH 4.6. Flasks were inoculated with a suspension of conidia of *Penicillium cyclopium* Westling (IMI 229034) in Tween 20 0.02% (w/v) to a final concentration of $5 \times 10^4$ conidia/mL., and the cultures were grown at 25° C. with 150 rpm rotary shaking. The addition to the medium of different extracts or fractions to be assayed for conidiation-inducing activity, as methanolic or ethanolic solutions, rendered final organic solvent concentrations lower than 0.5% (v/v), which did not influence the pattern of growth or conidiation. Determination of conidiation inducing activity was followed by microscopic observation of mycelium samples taken at different times. For these purposes, conidiation time was defined as the time at which 50% of the hyphal tips attained the final stage of conidiation (conidia-bearing tips), according to previously established criteria (Ugalde and Pitt, 1983), namely, the direct microscopic observation of three separate groups of 500 hyphal tips, and the determination of the proportion of hyphal tips in each group which bear conidia.

The above-described bioassay is based on the advancement in conidiation occurring when the medium contains any factor able to promote this morphogenetic process, with respect to that observed in a reference fresh F medium lacking this activity. Thus, for a fixed inoculum, there a two temporal limits concerning conidiation. The higher limit occurs when there is no conidiogenic inducer present in the medium (fresh medium), requiring the organism to produce all the inducer to reach the threshold concentration. The lower limit results from the presence from the beginning of the culture of threshold levels of inducer, so directly proceeding to conidiation induction without the need for additional inducer production. The lower limit often coincides with the time of germination. For intermediate values, the time in which conidiation occurs may be related to the inducer concentration present in the medium, between zero and the threshold concentration. The threshold concentration is defined as the minimum concentration (singly or in combination) of conidiogenol and/or conidiogenone required to induce conidiation, and for *Penicillium cyclopium*, it has been found that this threshold concentration is in the range of 50–125 ng/mL.

FIG. 1 depicts in bar graph format the results of experimental Examples 2–5, i.e., it depicts the conidiation response of a culture of the fungus *Penicillium cyclopium* induced by two different concentrations of both conidiogenol and conidiogenone, each of which was extracted, isolated and purified from *Penicillium cyclopium* in accordance with Example 1. Conidiation was measured at 28 hours after inoculation as the percent of conidium-bearing hyphal tips. By 28 hours after inoculation, a control culture without any conidiogenol or conidiogenone added did not conidiate. In contrast, when either of those compounds was added to the medium at the moment of inoculation, the levels of conidiation reached at 28 hours after inoculation surpassed 80%.

EXAMPLES 6–11

The bioassay procedure described above was used to assess qualitatively in other species of the genus Penicillium the conidiation-inducing activity of the compounds that were extracted, isolated and purified from *Penicillium cyclopium* in accordance with Example 1. Specifically, the same procedure was used as in Examples 2–5, with the same ingredients, except that it was performed each time with a concentration (singly or in combination) of conidiogenol and/or conidiogenone of approximately 250 ng/mL. (deliberately well in excess of the above-mentioned threshold concentration for induction of conidiation), and it was performed separately with cultures of each of the following species: *Penicillium notatum, P. italicum, P. spinulosum, P. luteum, P. thomii* and *P. oxalicum*. In each of these species positive activity was recorded, i.e., each species presented a conidiation pattern (>50% conidiating hyphal tips) at or before 24 hours of incubation in the presence of both compounds.

EXAMPLES 12–17

The purification procedure described above was used to assess whether conidiogenol and conidiogenone are produced in other species of the genus Penicillium. Specifically, the same procedure was used as in Example 1, with the same ingredients, except that it was performed separately with cultures of each of the following species: *Penicillium notatum, P. italicum, P. spinulosum, P. luteum, P. thomii* and *P. oxalicum*, and in each case the fermentation volumes from which the purification procedure was performed were 2 L.

All of these Penicillium species produced the same two molecules as did *Penicillium cyclopium* in Example 1, although the quantities obtained of both molecules were insufficient to undertake the same complete chemical analyses (such as NMR spectroscopy) as were performed in the case of the samples obtained from *Penicillium cyclopium* in Example 1. Nevertheless, it is believed that these species produced the same molecules as *P. cyclopium*, and not analogs or derivatives thereof, for the following reason. Cultures of *P. cyclopium* were exposed to the purified extracts from these other microorganisms in a proportion which would contain a combined concentration of conidiogenol and conidiogenone of approximately 250 ng/mL. (again deliberately well in excess of the above-mentioned threshold concentration for induction of conidiation). That proportion was achieved by administering the purified extracts in amounts which corresponded to five times the culture volumes from which they were obtained. The other conditions of these tests were otherwise identical to those used in Examples 2–5. All samples presented positive conidiogenic activity (>50% conidiating hyphal tips at or before 24 hours of incubation) when tested under identical conditions as were the compounds extracted from *P. cyclopium*, while no conidiation was observed in the control cultures at any time up to 48 hours of incubation.

These qualitative bioassay results, in light of the specificity of action of these extracts and the extremely low concentrations used, are believed sufficient to justify the conclusion that the same two molecules (conidiogenol and conidiogenone) are produced by any strain of microorganism belonging to the genus Penicillium. Further, the results of the experiments described in Examples 6–11 are believed sufficient to justify the conclusion that when these two molecules (conidiogenol and conidiogenone) are produced by any strain of microorganism belonging to the genus Penicillium, they can be utilized to induce conidiation not only in the producer strain, but in any one or more of the other strains of microorganism belonging to the genus Penicillium.

EXAMPLES 18–19

The bioassay procedure described above was used to assess qualitatively in other filamentous fungi, in particular, those of the genus Aspergillus, the conidiation-inducing activity of the compounds that were extracted, isolated and purified from *Penicillium cyclopium* in accordance with Example 1. Specifically, the same procedure was used as in Examples 2–5, with the same ingredients, except that it was performed with the species *Aspergillus nidulans* and the bioassay procedure was modified to accommodate the morphological characteristics of the conidiation process as it occurs in species of the genus Aspergillus. Thus, the criteria employed to determine the time of conidiation in these cases was the appearance of at least two conidiophores (the specific phialide bearing structure for this genus) on average per mycellial pellet, measured from a minimum of 10 pellets. The addition to the culture medium of 25–50 ng/mL of conidiogenone in one case, and 100 ng/mL of conidiogenol in the other case, resulted in positive conidiogenic activity after only 22 hours of incubation, while the control cultures did not display conidiation until at least 28 hours of incubation.

Therefore, conidiogenol and conidiogenone present activity in Aspergillus similar to that which they present in Penicillium, and these qualitative bioassay results are believed sufficient to justify the conclusion that the same two molecules are also synthesized by any strain of microorganism belonging to the genus Aspergillus, since it is considered unlikely that conidiation would be induced in one of those strains by "foreign" molecules (i.e., by molecules produced in *P. cyclopium*) unless the same two molecules (or very similar analogs) were also endogenous to Aspergillus strains. Further, on the basis of these results it is considered likely that the same two molecules (or related analogs) are produced in and/or act upon a wider range of fungi, and that they can be utilized to induce con idiation not only in the producer strain, but in one or more other strains of filamentous fungi as well, from a number of different genera, although it is believed that the threshold concentration required to induce conidiation may vary somewhat from strain to strain within each species, and is likely to vary more widely from species to species within each genus, with even wider variations possible from genus to genus.

Although their use as conidiation inducers in a fungus belonging to the genus Penicillium or the genus Aspergillus are the preferred applications of the invention, the scope of applicability of the invention is not limited to such uses; all kinds of compositions comprising conidiogenol or conidiogenone, even if intended for other applications, fall within the scope of the invention. Thus, while there has been described what are at present considered to be the preferred embodiments of the present invention, it will be apparent to those skilled in the art that the embodiments described herein are by way of illustration and not of limitation, and that various changes and modifications may be made therein without departing from the true spirit and scope of the present invention, as set forth in the appended claims.

REFERENCES CITED

The following publications were referenced herein, and the disclosures of these publications in their entireties are hereby incorporated by reference herein, to the same extent as if each individual publication were specifically and individually indicated to be incorporated by reference, in order to more fully describe the state of the art to which this invention pertains, and in order to more fully indicate the level of those skilled in the art to which the invention pertains:

1. Adams, T. H., Boylan, M. T. and Timberlake, W. E. (1988) *Cell*, 54, 353–362.
2. Clutterbuck, A. J. (1969) *Genetics*, 63, 317–327.
3. Foster, J. W., McDaniel, L. E., Woodruff, H. B. and Stokes, J. L. (1945) *J. Bacteriol.*, 50, 365–368.
4. Galbraith, J. C. and Smith, J. E. (1969) *J. Gen. Microbiol.*, 59, 31–45.
5. Hadley, G. & Harrold, C. E. (1958) *J. Exp. Bot.*, 9, 418–425.
6. Heath, I. B., ed. (1990) *Tip growth in plant and fungal cells*. Academic Press, San Diego, Calif.
7. Klebs, G. (1896) *Die bedingungen der fortphlanzung bei enigen algen und pilzen*. Jena: Verlag von Gustav Fischer.
8. Mirabito, P. M., Adams, T. H. & Timberlake, W. E. (1989) *Cell*, 57, 859–868.
9. Morton, A. G. (1961) *Proc. R. Soc. London Ser. B*, 153, 548–569.
10. Pascual, S., Melgarejo, P. and Magan, N. (1997) *Appl. Microbiol. Biotechnol.*, 48, 389–392.
11. Smith, J. E. and Berry, D. R. (1974) *An introduction to biochemistry of fungal development*. Academic Press, London, N.Y.
12. Ugalde, U. O. and Pitt, D. (1983) *Trans. Br. Mycol. Soc.*, 80, 319–325.
13. Wieser, J., Lee, B. N., Fondon, J. W. and Adams, T. H. (1994) *Curr. Genet.*, 27, 62–69.

What is claimed is:

1. A method for regulating the development of at least one filamentous fungal microorganism, said method comprising applying to a population of said at least one microorganism a compound having the formula

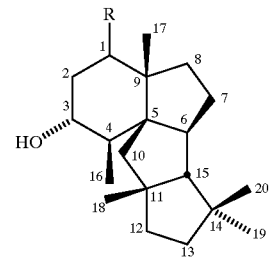

said compound being applied to said population in an amount effective to induce conidiation in or to inhibit the growth of said population or both.

2. The method of claim 1, wherein, in the compound of said formula, R is —OH.

3. The method of claim 1, wherein, in the compound of said formula, R is =O.

4. The method of claim 1, wherein said at least one microorganism comprises at least one species belonging to a genus selected at the group consisting of the genus Penicillium and the genus Aspergillus.

5. The method of claim 4, wherein said at least one species is selected from the group consisting of *Penicillium* cyclopium, *Penicillium notatum, Penicillium italicum, Penicillium spinulosum, Penicillium luteum, Penicillium thomii, Penicillium oxalicum* and *Aspergillus nidulans.*

6. The method of claim 5, wherein said compound originates from *Penicillium cyclopium*.

7. A method of regulating the development of at least one filamentous fungal microorganism, said method comprising applying to a population of said at least one microorganism a compound selected from the group consisting of (1R*, 3R*, 7R*, 8S*, 11R*, 12R*, 14S*, 15R*)-3,6,6,11,15-pentamethyl-tetracyclo[9.4.0.0$^{1,8}$.0$^{3,7}$]-pentadecan-12,14-diol and (1R*, 3R*, 7R*, 8S*, 11R*, 14S*, 15R*)-14-Hydroxy-3,6,6,11,15- pentamethyl-tetracyclo[9.4.0.0$^{1,8}$.0$^{3,7}$]-pentadecan-12-one, said compound being applied to said population in an amount effective to induce conidiation in or to inhibit the growth of said population or both.

8. The method of claim 7, wherein said compound is (1R*, 3R*, 7R*, 8S*, 11R*, 12R*, 14S*, 15R*)-3,6,6,11,15-pentamethyl-tetracyclo[9.4.0.0$^{1,8}$.0$^{3,7}$]-pentadecan-12,14-diol.

9. The method of claim 7, wherein said compound is (1R*, 3R*, 7R*, 8S*, 11R*, 14S*, 15R*)-14-Hydroxy-3,6,6,11,15-pentamethyl-tetracyclo[9.4.0.0$^{1,8}$.0$^{3,7}$]-pentadecan-12-one.

10. The method of claim 7, wherein said at least one microorganism comprises at least one species belonging to a genus selected from the group consisting of the genus Penicillium and the genus Aspergillus.

11. The method of claim 10, wherein said at least one species is selected from the group consisting of *Penicillium cyclopium, Penicillium notatum, Penicillium italicum, Penicillium spinulosum, Penicillium luteum, Penicillium thomii, Penicillium oxalicum* and *Aspergillus nidulans.*

12. The method of claim 11, wherein said compound originates from *Penicillium cyclopium*.

13. A method of inducing conidiation in at least one filamentous fungal microorganism, said method comprising applying to a population of said at least one microorganism a compound having the formula

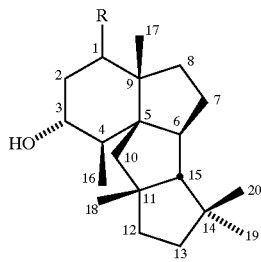

said compound being applied to said population in an amount effective to induce conidiation in said population.

14. The method of claim 13, wherein, in the compound of said formula, R is —OH.

15. The method of claim 13, wherein, in the compound of said formula, R is =O.

16. The method of claim 13, wherein said at least one microorganism comprises at least one species belonging to a genus selected from the group consisting of the genus Penicillium and the genus Aspergillus.

17. The method of claim 16, wherein said at least one species is selected from the group consisting of *Penicillium cyclopium, Penicillium notatum, Penicillium italicum, Penicillium spinulosum, Penicillium luteum, Penicillium thomii, Penicillium oxalicum* and *Aspergillus nidulans.*

18. The method of claim 17, wherein said compound originates from *Penicillium cyclopium*.

19. A method of inducing conidiation in at least one filamentous fungal microorganism, said method comprising applying to a population of said at least one microorganism a compound selected from the group consisting of (1R*, 3R*, 7R*, 8S*, 11R*, 12R*, 14S*, 15R*)-3,6,6,11,15-pentamethyl-tetracyclo[9.4.0.0$^{1,8}$.0$^{3,7}$]-pentadecan-12,14-diol and (1R*, 3R*, 7R*, 8S*, 11R*, 14S*, 15R*)-14-Hydroxy-3,6,6,11,15-pentamethyl-tetracyclo[9.4.0.0$^{1,8}$.0$^{3,7}$]-pentadecan-12-one, said compound being applied to said population in an amount effective to induce conidiation in said population.

20. The method of claim 19, wherein said compound is (1R*, 3R*, 7R*, 8S*, 11R*, 12R*, 14S*, 15R*)-3,6,6,11,15-pentamethyl-tetracyclo[9.4.0.0$^{1,8}$.0$^{3,7}$]-pentadecan-12,14-diol.

21. The method of claim 19, wherein said compound is (1R*, 3R*, 7R*, 8S*, 11R*, 14S*, 15R*)-14-Hydroxy-3,6,6,11,15-pentamethyl-tetracyclo[9.4.0.0$^{1,8}$.0$^{3,7}$]-pentadecan-12-one.

22. The method of claim 19, wherein said at least one microorganism comprises at least one species belonging to a genus selected from the group consisting of the genus Penicillium and the genus Aspergillus.

23. The method of claim 22, wherein said at least one species is selected from the group consisting of *Penicillium cyclopium, Penicillium notatum, Penicillium italicum, Penicillium spinulosum, Penicillium luteum, Penicillium thomii, Penicillium oxalicum* and *Aspergillus nidulans.*

24. The method of claim 23, wherein said compound originates from *Penicillium cyclopium*.

25. A method of inhibiting the growth of at least one filamentous fungal microorganism, said method comprising applying to a population of said at least one microorganism a compound having the formula

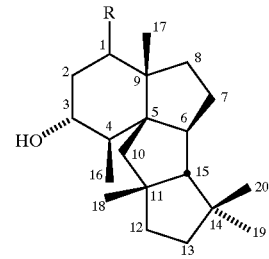

said compound being applied to said population in an amount effective to inhibit the growth of said population.

26. The method of claim 25, wherein, in the compound of said formula, R is —OH.

27. The method of claim 25, wherein, in the compound of said formula, R is =O.

28. The method of claim 25, wherein said at least one microorganism comprises at least one species belonging to a genus selected from the group consisting of the genus Penicillium and the genus Aspergillus.

29. The method of claim 28, wherein said at least one species is selected from the group consisting of *Penicillium cyclopium, Penicillium notatum, Penicillium italicum, Penicillium spinulosum, Penicillium luteum, Penicillium thomii, Penicillium oxalicum* and *Aspergillus nidulans.*

30. The method of claim 29, wherein said compound originates from *Penicillium cyclopium*.

31. A method of inhibiting the growth of at least filamentous fungal microorganism, said method comprising applying to a population of said at least one microorganism a compound selected from the group consisting of (1R*, 3R*, 7R*, 8S*, 11R*, 12R*, 14S*, 15R*)-3,6,6,11,15-pentamethyl-tetracyclo[9.4.0.0$^{1,8}$.0$^{3,7}$]-pentadecan-12,14-diol and (1R*, 3R*, 7R*, 8S*, 11R*, 14S*, 15R*)-14-Hydroxy-3,6,6,11,15-pentamethyl-tetracyclo[9.4.0.0$^{1,8}$.0$^{3,7}$]-pentadecan-12-one, said compound being applied to said population in an amount effective to inhibit the growth of said population.

32. The method of claim 31, wherein said compound is (1R*, 3R*, 7R*, 8S*, 11R*, 12R*, 14S*, 15R*)-3,6,6,11,15-pentamethyl-tetracyclo[9.4.0.0$^{1,8}$.0$^{3,7}$]-pentadecan-12,14-diol.

33. The method of claim 31, wherein said compound is (1R*, 3R*, 7R*, 8S*, 11R*, 14S*, 15R*)-14-Hydroxy-3,6,6,11,15-pentamethyl-tetracyclo[9.4.0.0$^{1,8}$.0$^{3,7}$]-pentadecan-12-one.

34. The methods of claim 31, wherein said at least one microorganism comprises at least one species belonging to a genus selected from the group consisting of the genus Penicillium and the genus Aspergillus.

35. The method of claim 34, wherein said at least one species is selected from the group consisting of *Penicillium cyclopium, Penicillium notatum, Penicillium italicum, Penicillium spinulosum, Penicillium luteum, Penicillium thomii, Penicillium oxalicum* and *Aspergillus nidulans*.

36. The method of claim 35, wherein said compound originates from *Penicillium cyclopium*.

* * * * *